US010993627B1

(12) United States Patent
Dotter

(10) Patent No.: US 10,993,627 B1
(45) Date of Patent: May 4, 2021

(54) DEVICE FOR DETERMINING BLOOD PRESSURE WITHOUT A CUFF

(71) Applicant: James Eric Dotter, Boulder, CO (US)

(72) Inventor: James Eric Dotter, Boulder, CO (US)

( * ) Notice: Subject to any disclaimer, the term of this patent is extended or adjusted under 35 U.S.C. 154(b) by 0 days.

(21) Appl. No.: 15/873,824

(22) Filed: Jan. 17, 2018

Related U.S. Application Data

(60) Provisional application No. 62/449,926, filed on Jan. 24, 2017.

(51) Int. Cl.
*A61B 5/021* (2006.01)
*A61B 5/024* (2006.01)

(52) U.S. Cl.
CPC ...... *A61B 5/02116* (2013.01); *A61B 5/02141* (2013.01); *A61B 5/02416* (2013.01); *A61B 2562/04* (2013.01)

(58) Field of Classification Search
CPC ............ A61B 5/02116; A61B 5/02141; A61B 5/02416; A61B 2562/04; A61B 5/02125; A61B 5/02255; A61B 5/0535; A61B 5/0295
See application file for complete search history.

(56) References Cited

U.S. PATENT DOCUMENTS

| | | | | |
|---|---|---|---|---|
| 5,379,774 A * | 1/1995 | Nishimura | ......... | A61B 5/02007 600/479 |
| 5,862,805 A * | 1/1999 | Nitzan | ............... | A61B 5/02416 128/898 |
| 6,120,459 A * | 9/2000 | Nitzan | ............... | A61B 5/02125 600/485 |
| 7,544,168 B2 * | 6/2009 | Nitzan | ................... | A61B 5/021 600/485 |
| 7,674,231 B2 * | 3/2010 | McCombie | ........ | A61B 5/02125 600/481 |
| 9,060,695 B2 * | 6/2015 | Peters | ................. | A61B 5/14552 |
| 10,085,652 B2 * | 10/2018 | Baek | ...................... | A61B 5/021 |
| 10,194,862 B2 * | 2/2019 | Chakravarthi | ....... | A61B 5/0022 |
| 10,213,117 B2 * | 2/2019 | Lading | .................... | A61B 5/026 |
| 10,292,662 B2 * | 5/2019 | Kirenko | .................. | G06T 7/254 |
| 10,398,328 B2 * | 9/2019 | Kirenko | ............. | A61B 5/14552 |
| 10,448,848 B2 * | 10/2019 | Park | ................... | A61B 5/14551 |
| 10,517,487 B2 * | 12/2019 | Naghavi | ............ | A61B 5/02028 |
| 10,772,512 B2 * | 9/2020 | Klaassen | ................ | A61B 5/681 |
| 2002/0169380 A1 * | 11/2002 | Hasegawa | .......... | A61B 5/02116 600/485 |
| 2003/0199771 A1 * | 10/2003 | Baruch | .............. | A61B 5/02416 600/485 |

(Continued)

OTHER PUBLICATIONS

Chan, Gabriel et al. "Multi-Site Photoplethysmography Technology for Blood Pressure Assessment: Challenges and Recommendations." Journal of clinical medicine vol. 8,11 1827. Nov. 1, 2019, doi:10.3390/jcm8111827 (Year: 2019).*

(Continued)

*Primary Examiner* — John Villecco

(57) ABSTRACT

A device and method to obtain accurate blood pressure measurement without a cuff, using a plurality of PPG sensors, in a non-clinical setting; that is, without the measurement being administered by a medically trained person. Unique and novel elements make this possible by eliminating the confounding effects of gravity in cases where the lay user is not careful to position the device at a specific or consistent elevation relative to that of the heart.

1 Claim, 7 Drawing Sheets

(56) References Cited

U.S. PATENT DOCUMENTS

| | | | | |
|---|---|---|---|---|
| 2006/0020216 A1* | 1/2006 | Oishi | A61B 5/0205 | 600/500 |
| 2006/0122520 A1* | 6/2006 | Banet | A61B 5/021 | 600/503 |
| 2006/0217615 A1* | 9/2006 | Huiku | A61B 5/08 | 600/484 |
| 2007/0225614 A1* | 9/2007 | Naghavi | A61B 5/02007 | 600/549 |
| 2007/0276262 A1* | 11/2007 | Banet | A61B 5/02255 | 600/485 |
| 2008/0081963 A1* | 4/2008 | Naghavi | A61B 5/6806 | 600/301 |
| 2008/0221461 A1* | 9/2008 | Zhou | A61B 5/021 | 600/485 |
| 2011/0054277 A1* | 3/2011 | Pinter | A61B 5/02438 | 600/310 |
| 2012/0029320 A1* | 2/2012 | Watson | A61B 5/02416 | 600/301 |
| 2012/0029363 A1* | 2/2012 | Lund | A61B 5/02108 | 600/485 |
| 2013/0046192 A1* | 2/2013 | Lin | A61B 5/02007 | 600/500 |
| 2013/0137938 A1* | 5/2013 | Peters | A61B 5/02125 | 600/301 |
| 2014/0106816 A1* | 4/2014 | Shimuta | G06F 3/04883 | 455/556.1 |
| 2014/0114201 A1* | 4/2014 | Watanabe | H04R 1/2807 | 600/485 |
| 2014/0276123 A1* | 9/2014 | Yang | A61B 5/7275 | 600/483 |
| 2015/0073239 A1* | 3/2015 | Pei | A61B 5/14551 | 600/324 |
| 2015/0119725 A1* | 4/2015 | Martin | A61B 5/04012 | 600/479 |
| 2016/0022157 A1* | 1/2016 | Melker | A61B 5/02108 | 600/407 |
| 2017/0007184 A1* | 1/2017 | Kang | A61B 5/02035 | |
| 2017/0014036 A1* | 1/2017 | Kang | A61B 5/6825 | |
| 2017/0078036 A1* | 3/2017 | Lee | H04J 3/06 | |
| 2017/0079591 A1* | 3/2017 | Gruhlke | A61B 5/6898 | |
| 2017/0105633 A1* | 4/2017 | Shin | A61B 5/681 | |
| 2017/0164904 A1* | 6/2017 | Kirenko | G06T 7/20 | |
| 2017/0238818 A1* | 8/2017 | Gaurav | A61B 5/02125 | |
| 2017/0340219 A1* | 11/2017 | Sullivan | A61B 5/02125 | |
| 2017/0367614 A1* | 12/2017 | Zuckerman-Stark | A61B 5/6831 | |
| 2018/0070837 A1* | 3/2018 | Huijbregts | A61B 5/02255 | |
| 2018/0085011 A1* | 3/2018 | Ma | A61B 5/7203 | |
| 2018/0098731 A1* | 4/2018 | Yoon | A61B 5/0205 | |
| 2018/0199869 A1* | 7/2018 | Huiku | A61B 5/7278 | |
| 2018/0206735 A1* | 7/2018 | Holz | A61B 5/6803 | |
| 2018/0279965 A1* | 10/2018 | Pandit | A61B 5/7225 | |
| 2019/0076032 A1* | 3/2019 | Park | A61B 5/6885 | |
| 2019/0142286 A1* | 5/2019 | Mouradian | A61B 5/021 | |
| 2019/0175031 A1* | 6/2019 | Noronha | A61B 5/6806 | |
| 2019/0254524 A1* | 8/2019 | Granqvist | G16H 50/30 | |
| 2019/0269338 A1* | 9/2019 | Harris | A61B 7/02 | |
| 2019/0307337 A1* | 10/2019 | Little | A61B 5/332 | |
| 2019/0313917 A1* | 10/2019 | Xu | A61B 5/02416 | |
| 2020/0000349 A1* | 1/2020 | Lin | A61B 5/6841 | |
| 2020/0187789 A1* | 6/2020 | Naghavi | A61B 5/318 | |
| 2020/0187809 A1* | 6/2020 | Larsen | A61B 5/02108 | |
| 2020/0245880 A1* | 8/2020 | Choi | A61B 5/7235 | |
| 2020/0305736 A1* | 10/2020 | Monti | A61B 5/02116 | |
| 2020/0367760 A1* | 11/2020 | Klaassen | A61B 5/681 | |

OTHER PUBLICATIONS

Nabeel PM, Karthik S, Joseph J, Sivaprakasam M. "Measurement of carotid blood pressure and local pulse wave velocity changes during cuff induced hyperemia"; Annu Int Conf IEEE Eng Med Biol Soc. 2017;2017:1700-1703. doi:10.1109/EMBC.2017.8037169 (Year: 2017).*

Nabeel PM, Jayaraj J, Mohanasankar S. Single-source PPG-based local pulse wave velocity measurement: a potential cuffless blood pressure estimation technique. Physiol Meas. Nov. 30, 2017;38(12):2122-2140. doi: 10.1088/1361-6579/aa9550. PMID: 29058686. (Year: 2017).*

Nabeel PM, Joseph J, Awasthi V, Sivaprakasam M. "Single source photoplethysmograph transducer for local pulse wave velocity measurement". Annu Int Conf IEEE Eng Med Biol Soc. 2016;2016:4256-4259. doi: 10.1109/EMBC.2016.7591667 (Year: 2016).*

* cited by examiner the arrival of the pulse wave at a point distant from the heart, such as a fingertip, as measured by the PPG. The measured elapsed time (PTT), along with the length of the arm, is then used in attempts to calculate a PWV, and from that a systolic blood pressure.
DEVICE FOR DETERMINING BLOOD PRESSURE WITHOUT A CUFF

BACKGROUND

There exists prior art describing the inclusion of an ECG monitoring circuit designed into a device. Likewise, prior art exists describing the inclusion of a PPG (photoplethysmography) monitoring circuit in a device. These devices have been used to measure and record heart rate, and other related data derived from the analysis of heart beats as related one to the next, including respiratory rate and heart-rate variability (HRV).

Prior art also describes using a combination of ECG and PPG pulse wave detection to calculate a Pulse Transit Time (PTT), and the relationship between PTT and blood pressure is well established. For example, U.S. Pat. Nos. 5,316,008; 5,857,975; 5,865,755; and 5,649,543 each describe an apparatus that includes conventional sensors that measure an ECG and PPG, which are then processed to determine PIT. Pulse Wave Velocity (PWV) is measured by combining an ECG signal and a PPG signal. The elapsed time is measured between the R-point of the ECG for a given heart beat, and the arrival of the pulse wave at a point distant from the heart, such as a fingertip, as measured by the PPG. The measured elapsed time (PTT), along with the length of the arm, is then used in attempts to calculate a PWV, and from that a systolic blood pressure.

Some of this has been used effectively in clinical settings where a patient is in a controlled environment, the measurement is administered by a trained medical person, and the effect of posture and gravity can thus be neutralized or accounted for.

In a non-clinical setting however, in which an untrained or lay user initiates the measurement, the challenge of neutralizing the effect of gravity has limited the usefulness of PWV-based solutions. The effect of gravity is to artificially increase PWV when the PPG measurement point, such as a fingertip, is held below the level of the heart, and to decrease PWV when that same point is held above the heart; the compression wave is working either with or against gravity as it travels from the heart to the measurement point. This has frustrated efforts to use PTT, and by extension, photoplethysmography, to obtain accurate blood pressure readings in devices for use by lay-persons, without the trouble and complexity of a blood pressure (BP) cuff and related apparatus.

THE GIST OF THE INVENTION

Figure 1:
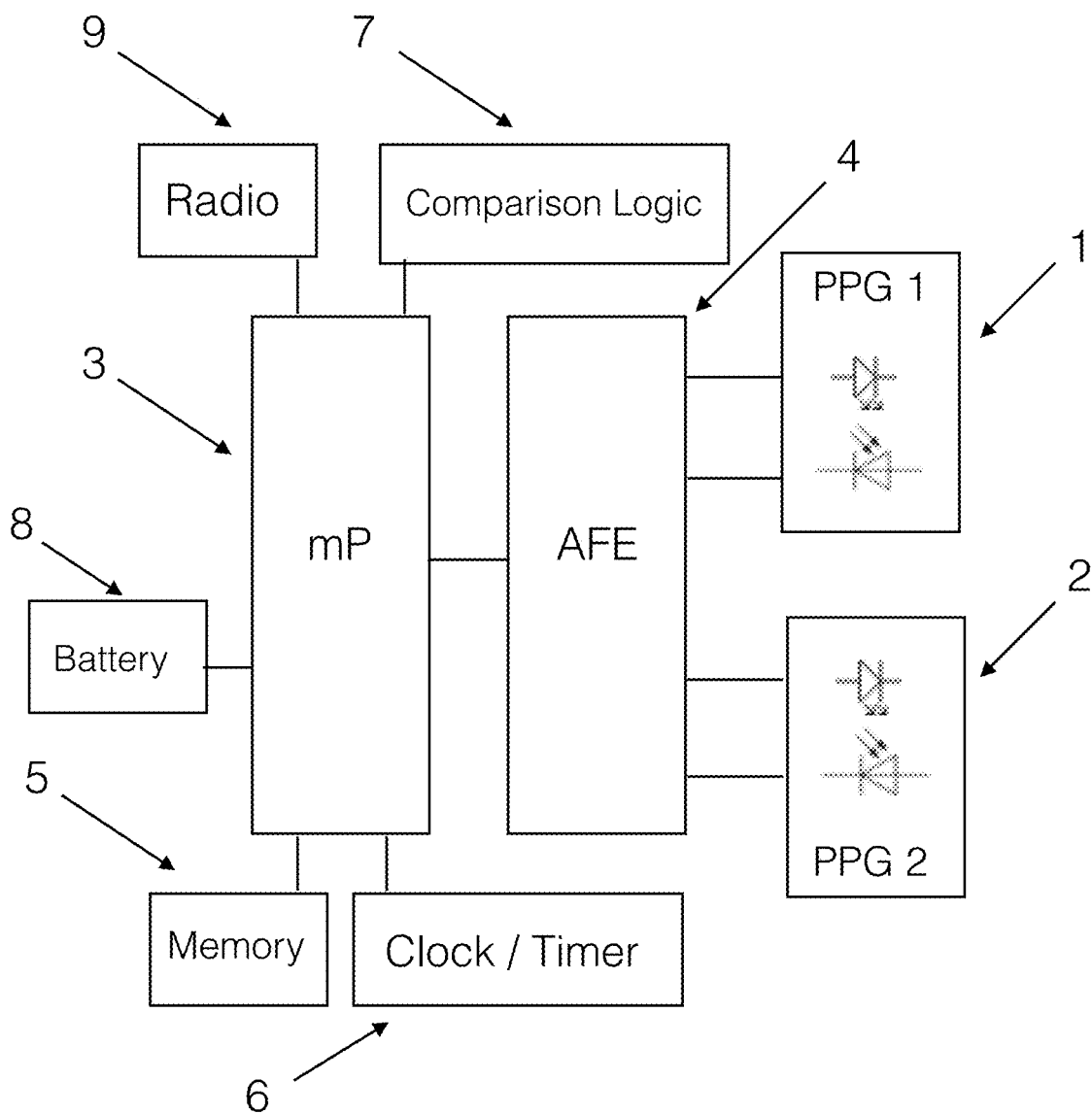
FIG. 1 presents a block diagram of the major electronic elements of the device. A microprocessor 3 connected to an analog front end 4 that is connected to two photoplethysmography sensors (PPGs) 1 and 2 to provide the essential measurement functions. Also shown, a clock/timer circuit 6, special comparison logic 7, a battery 8, memory 5, and an optional radio 9 support these functions.

This invention teaches a device and method to easily obtain accurate blood pressure measurement without a cuff, in a non-clinical setting; that is, without the measurement being administered by a medically trained person. Unique and novel elements make this possible by eliminating the confounding effects of gravity, in cases where the lay user is not careful to position the device, and thus the measurement points, at a specific or consistent elevation relative to that of the heart.

The invention consists of a device that includes at least two PPG measurement sensors and circuits, described herein as PPG1 and PPG2, and further also includes a microprocessor, memory, an analog front end, and a precise timing function, and further includes logic to precisely measure the elapsed time between events and characteristics in the datastreams of the aforesaid sensors (PPG1, PPG2) with respect to each other, such that specialized logic can compare features within the at least two measurements in terms of the time differential between a feature of the data of one measurement and a feature of the data of another measurement. Given a precise timing between these data features, and given signal amplitudes and other information pertinent to the user, a calculation of blood pressure can be obtained without regard to the user's inconsistent positioning of the device relative to the level of the heart.

The device is further designed to bring the first PPG, numbered item 1 in FIGS. 1 through 7, and referenced below as PPG1, into a position allowing it to be in contact or proximity with a "preferred first measurement site", such as a fingertip or thumb tip of the hand of the user. So designed and placed, PPG1 can monitor characteristics of a first pulse wave data stream at that measurement site, where each pulse wave is related to a specific heart beat. The precise timing of various characteristics of this first pulse wave data stream can be measured and stored. These characteristics include but are not limited to the first sign of arrival of the pulse wave associated with each heart beat, and also the amplitude of the signal. For the duration that the user holds the preferred first measurement site in contact with PPG1, a continuous stream of data can be obtained.

The device is further designed to make accessible to the user a second PPG (numbered item 2 in FIGS. 1 through 6, and referenced below as PPG2) in a position allowing it to be in contact or proximity to a user's preferred second measurement site, e.g. a finger tip or thumb tip not used as the preferred first measurement site, but of the same hand as the preferred first measurement site. This second PPG measures and records a second pulse wave data stream, in a manner similar to the first PPG, and synchronized with it, such that comparison can be made between characteristics of the first and second pulse waves, for the same heart beat or beats.

The device is designed to make at least two PPGs, able to be in contact with at least two digits of the same hand, for the period of time constituting a measurement.

Several exemplary embodiments are described here, which are not intended to limit the possible embodiments.

One exemplary embodiment of the device is for it to be designed to be placed on a wrist of the user, in the manner of a wristwatch or wristband. Referencing FIGS. 2 and 3, the device so placed and so configured brings the first PPG, numbered item 1 in the figures, and referenced below as PPG1, and the second PPG, numbered item 2 in the figures, and referenced below as PPG2, into locations allowing them to be in contact or proximity with the preferred first and second measurement sites, such as two digits of the same hand. In this embodiment, logic in the device can detect when the user has placed digits on both PPGs 1 and 2, and can initiate measuring and monitoring blood pressure.

Figure 2:
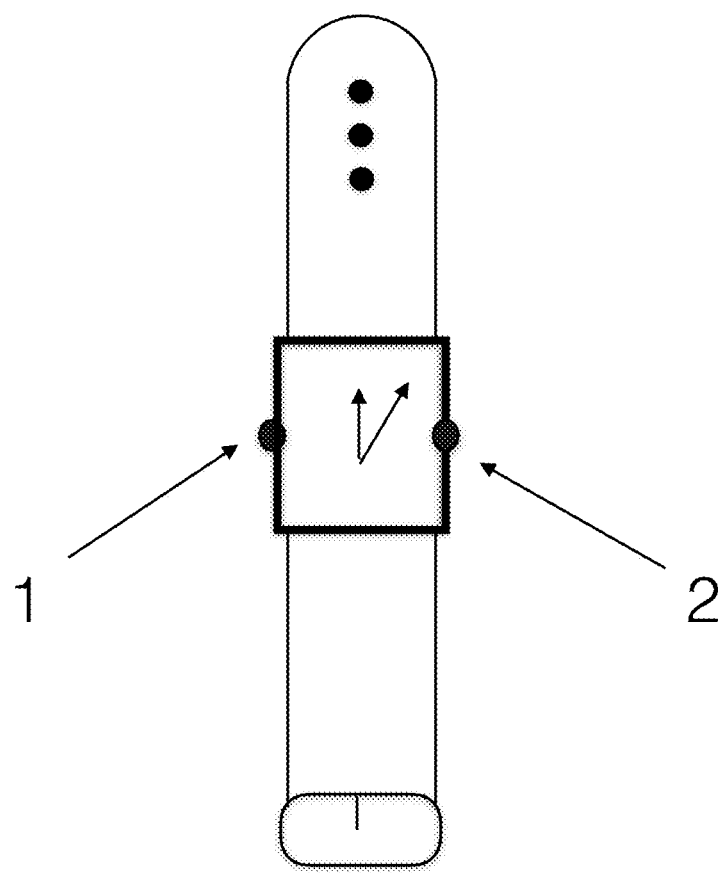
FIG. 2 presents one exemplary embodiment of the device, with a PPG sensor 1 on the side of the body of the device, and a second PPG sensor 2 on the other side.

In one exemplary embodiment, referencing FIG. 2, the first PPG (PPG1) (numbered item 1 in FIG. 2) is positioned on a side or edge of the wrist-mounted device, and fitted to facilitate placement of the user's preferred first measurement site (e.g. a thumb tip of the hand opposite the wrist upon which the device is worn) thereon. In this exemplary embodiment, the second PPG 2 is positioned on a different side or edge of the wrist mounted device, and fitted to facilitate placement of the user's preferred second measurement site (e.g. a fingertip of the hand opposite the wrist upon which the device is worn) thereon. Thus simultaneously obtaining measurements from the two digits.

Figure 3:
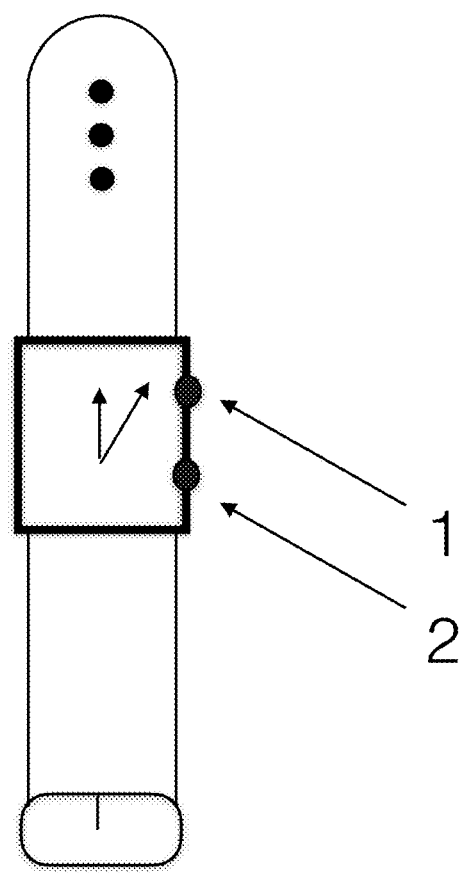
FIG. 3 presents another exemplary embodiment of the device, with a PPG sensor 1 on the side of the body of the device, and a second PPG sensor 2 on the same side.

In another exemplary embodiment, referencing FIG. 3, the PPG 1 and the PPG 2 are both positioned on the same side or edge of the wrist mounted device, to facilitate placement of the user's preferred first and second measurement sites (e.g. two fingertips of the opposite hand) thereon.

In yet another exemplary embodiment, the PPG1 and the PPG2 are both positioned on the top or face of the wrist mounted device, and fitted to facilitate placement of the user's preferred first and second measurement sites (e.g. fingertips of the opposite hand) thereon.

Figure 4:
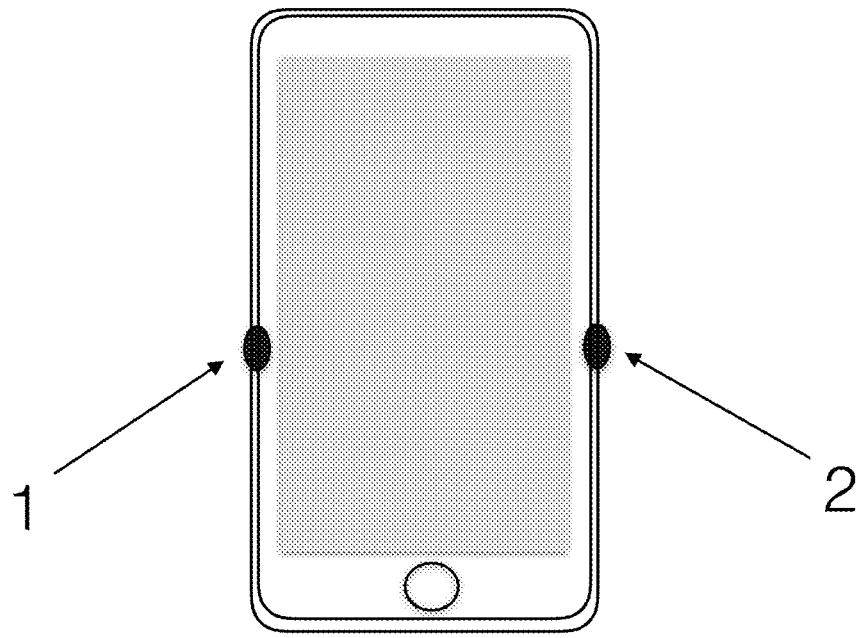
FIG. 4 presents another exemplary embodiment of the device, with a PPG sensor 1 on the side or edge of the body of a device designed to serve also as a mobile phone case, and a second PPG sensor 2 on another side or edge of the phone case.

In another exemplary embodiment, referencing FIG. 4, the device is designed to be a mobile phone or a mobile phone case. FIG. 4 illustrates a means by which the two PPGs 1 and 2 can be placed in a position allowing them to be in contact with two measurement sites (e.g. finger tip and thumb) of the hand which is holding the phone. Other electronic components can be built into the phone or phone case (not shown in FIG. 4). In this embodiment, the device can detect when measurement sites are in contact with PPGs 1 and 2 and can begin to measure and monitor blood pressure while the user uses the phone in the normal course of daily life, that is, without making a conscious decision to initiate a blood pressure measurement.

Figure 5:
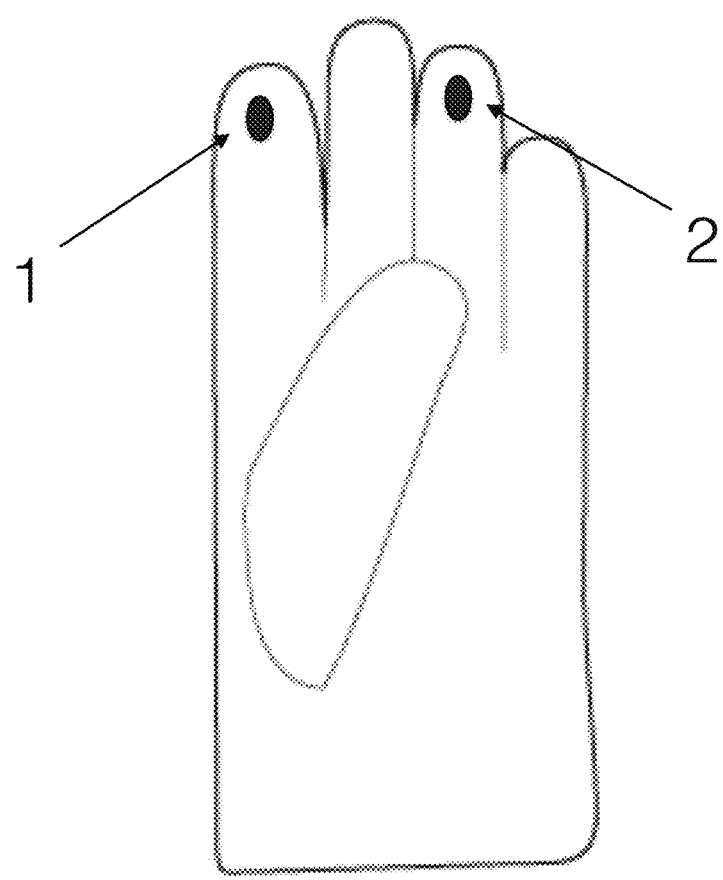
FIG. 5 presents another exemplary embodiment of the device, designed into a glove, with PPG sensor 1 positioned to be in contact with one measurement point (a finger tip) and PPG sensor 2 positioned to be in contact with the other measurement point (another finger tip) of the same hand.

In another exemplary embodiment, the device is designed into a glove. FIG. 5 illustrates the positioning of the two PPG sensors 1 and 2 within the glove, allowing them to be in contact with two measurement sites (e.g. finger and/or thumb tips) on the skin of the wearer, when the glove is worn. Other electronic components can be built into the glove (not shown in FIG. 5). In this embodiment, the blood pressure monitoring feature can be continuous while the glove is worn.

Figure 6:
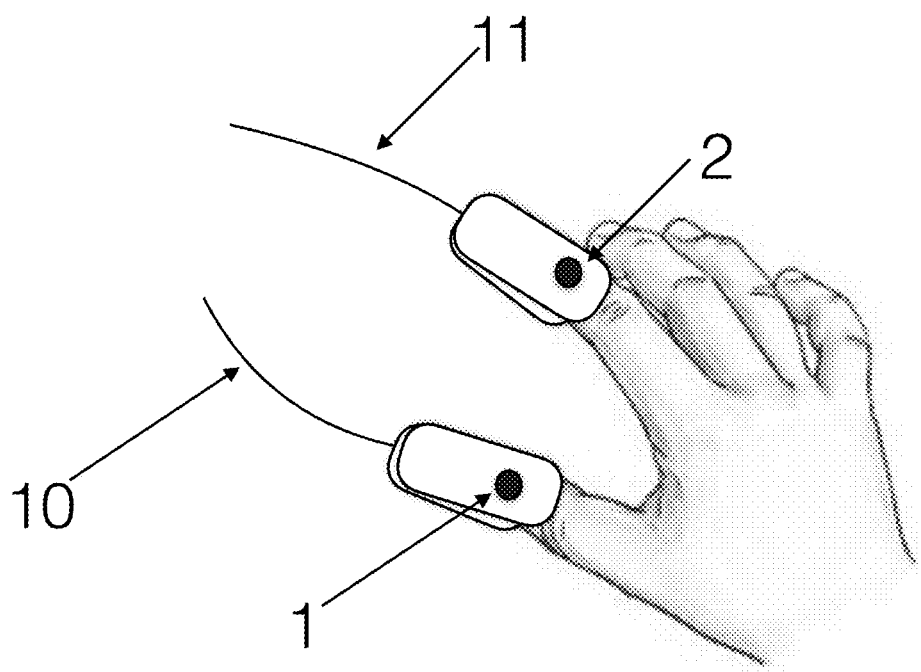
FIG. 6 presents another exemplary embodiment of the device, using two fingertip clips to make a PPG 1 and a second PPG 2 be in contact with the measurement points of two digits of the same hand.

In another exemplary embodiment, envisioned for a clinical setting, the device is designed to make use of two fingertip clips, of the style used in hospital pulse-oximetry devices. FIG. 6 illustrates the use of one fingertip clip with a PPG 1 and another fingertip clip with a PPG 2. Wires 10 and 11 lead to the other electronic components (not shown in FIG. 6). In this embodiment, the blood pressure monitoring feature can be continuous.

Figure 7:
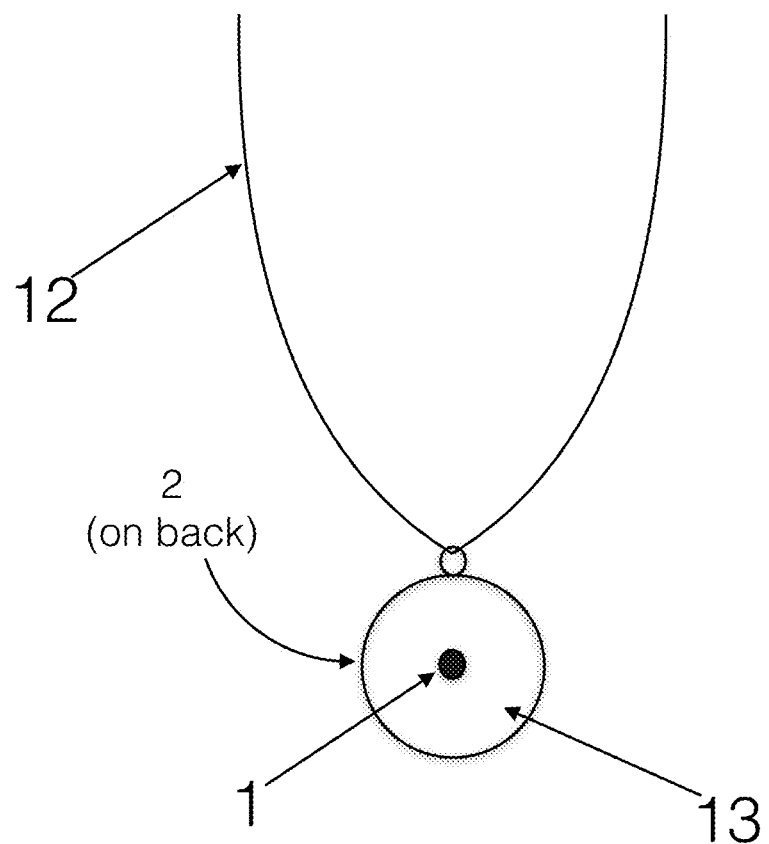
FIG. 7 presents another exemplary embodiment of the device, in which the electronics is built into a pendant 13, designed to be worn around the neck on a chain 12, with PPG sensor 1 on the face of the pendant, and PPG sensor 2 on the back of the pendant.

In another exemplary embodiment, referencing FIG. 7, the electronics and sensors are built into a pendant 13 to be worn about the neck on a chain 12. The first PPG 1 is mounted on one face of the pendant, while the second PPG 2 is mounted on the back surface of the pendant, such that the user can grasp the pendant between the thumb and finger, and initiate a blood pressure reading.

Differential PWA

Differential Pulse Wave Analysis (Differential PWA) is the term used herein to describe a method for comparison of pulse wave characteristics of two different sites (i.e. fingertips or finger and thumb) of the same hand. In applying this method to obtain blood pressure (BP) data, it is important to understand some basics of how the arterial system functions. One obvious function is to transport oxygenated blood from the heart to the various tissues. Another important function is to convert a pulsatile systolic blood pressure at the aorta, created by ventricular contraction, into a more steady and constant arterial blood pressure at the capillaries. As a pulse or pulse wave progresses through the arterial tree to a given destination, such as a measurement site at the fingertip, each segment of the arterial tree contributes to the conditioning of the pulse. This is accomplished more or less well, depending on the degree of elasticity (also called compliance) of the arteries. Other factors equal, the greater the compliance, the lower the systolic BP. And the greater the arterial compliance, the greater the elapsed time of a pulse wave to reach a fingertip (also described as the slower the pulse transit time, or PTT).

In traditional explorations of PTT however, "other factors equal" is an impossible goal to reach. In particular, the Pulse Transit Time is a calculation affected by the compliance of the arterial system, mixed in with myriad other factors. These include: the relative strength of each ventricular contraction, the ejection fraction and other aspects of the performance of the heart; the behavior of the aorta, subclavian and brachial arteries, and of the aortic valve. The same is true of many other confounding factors related to the regulation of heart and large arteries, such as signals from baroreceptors in the aortic arch and the common carotid arteries that request adjustments to meet immediate demands of the system, such as when the subject suddenly stands up.

These and other variables create a very confusing picture for systems that rely on a single PPG, whether measuring PTT relative to an ECG R-wave, or just looking at the characteristics of the PPG wave itself. It becomes impossible to separate the causes of changes in PTT, and therefore impossible to identify any specific changes indicative of relative arterial compliance, which is directly related to blood pressure.

Each digit is fed by an arterial path, and much of that path is common to all digits of a hand. But each digit has in its path some set of arterial segments different from the other digits. Differential PWA is an analysis of this system based on the understanding that any signal characteristics generated by the common elements listed above, including but certainly not limited to behavior of the ventricle, aorta, subclavian or brachial arteries, or of the aortic valve, will be common to all digits of the hand, and thus will be factored out as a common element of the two compared signals. Any remaining differences in the signal characteristics observed between two digits of the same hand, must be generated by the behavior of the arterial segments unique to those digits, the segments that those digits do not have in common.

Differential PWA thus isolates specific arterial segments for examination, and compares the signal characteristics of one segment with those of another segment. Especially pertinent to the goal of establishing blood pressure values, this isolates differences with respect to the effect that arterial compliance has on those signals.

With differential PWA measurement, all of the confounding variables are common to both of the signals, and are thus factored out.

To measure pulse wave timing difference, the microprocessor in the device identifies a pulse wave arriving at the preferred first measuring site (PPG1), then measures the elapsed time until the appearance of the associated pulse wave (from the same heartbeat) at the preferred second measurement site on the same hand (PPG2). If the elapsed time is outside of a threshold, indicating that these pulse waves are not generated by the same heartbeat, they are discarded, and measurement restarts until the two pulse waves are found to be generated by the same heartbeat.

In one exemplary implementation, a calibration step is used in which the user obtains a blood pressure reading via some other, trusted means, such as during a medical checkup where the medical person uses the cuff method (sphygmomanometry), and enters that reading into the device (or into a connected device such as an app on a connected smartphone) and, concurrently, uses the device of this invention to take a blood pressure reading in a calibration mode. The device (or connected app) computes a constant that can be saved on the device (or connected app). In subsequent operations of the device, these calibration values are used in combination with values from differential PWA readings to derive a precise blood pressure.

In another exemplary implementation, a second calibration step is taken, to obtain a non-trivially different systolic BP measurement from the first calibration measurement. The use of the two calibration points provides a very accurate means of then interpolating or extrapolating from measured PPG differences to a precise blood pressure value.

In yet another exemplary implementation, differential PWA measurements for an individual are compared to known behavior for a population of subjects of similar age, sex, height and weight, and conversion coefficients are derived from data related to these factors.

In yet another exemplary implementation, known behavior for a population as described above is combined with one or two calibration values, also described above, to further increase the precision of new readings.

Use of Differential PWA in this Invention to Factor Out the Effects of Gravity

This invention has the unique advantage over prior art of neutralizing the effect of gravity. By virtue of the fact that the device contains within it both PPG1 to measure the first pulse wave and PPG2 to measure the second pulse wave, these two measurement points are by necessity close together, and thus both at the same elevation with respect to the heart. For example, and referencing FIG. 2, one preferred embodiment places the PPG1 (FIG. 2, item 1) on one side of a wrist-watch body, and the PPG2 (FIG. 2 item 2) on the other side of the wrist-watch body, and in this configuration the first measurement site and the second measurement site are only as far apart as the watch-body width. The same can be said of embodiments shown in FIGS. 3 through 7.

Consider the computation of systolic blood pressure (BPsys) using traditional PTT between two measuring sites along an arterial path, without accounting for gravitational effect:

Given the following:

D=distance from the heart to measurement site 2−distance from the heart to measurement 1

PTT1=arrival time of a pulse wave, from ECG R-point, to PPG1

PTT2=arrival time of a pulse wave, of the same beat, from ECG R-Point, to PPG2

Then:

$$PWV=D/(PTT2-PTT1)$$

$$BPsys=PWV \times C1+C2$$

where C1 is a constant adjusting the slope, and C2 is a constant adjusting the y-intercept Now however, modeling in the effects of gravity on the two measurement points: assume a function g(E) which returns an adjustment due to gravity where E is the difference in elevation between the heart and the measurement point The calculation appears as follows:

$$PWV=D/((PTT2+g(E2))-(PTT1+g(E1))$$

where:

E1 is the elevation difference between heart and measurement point 1

E2 is the elevation difference between heart and measurement point 2

Now, if E2−E1=0, so too does G(E2)−G(E1)=0, and these terms can be factored out. This leaves the familiar:

$$PWV=D/(PTT2-PTT1)$$

as before, but now with the assurance that the effect of gravity is nil.

In this invention, using Differential PWA in an identical way to the above, two measurement sites are compared, and the effect of gravity is likewise factored out by virtue of the two measurement sites being positioned on the device as described, and thus in close proximity, such that the gravitational effect functions g(E1) and g(E2) return the same value, and drop out of the equation.

By positioning the two PPG measurement points close together in a device the invention assures that gravity affects data obtained from both measurement sites equally, therefore the gravitational effect is factored out of the calculation. In this way, an accurate measurement can be obtained without undue care to position the measuring device at a specific elevation relative to the heart, which is to say, without being administered by trained medical personnel.

It is unique and non-obvious to design a device with at least two PPG sensors, designed to read at least two different measurement points on the body, because pulse wave detecting PPG sensors measure the same data, that of heart beats and the timing between beats. It would be considered redundant by those skilled in the art to include more than one PPG sensor, and to position them to take measurements at two different locations not on the same arterial path.

The description of this invention teaches that by using Differential PWA, no ECG signal is needed to calculate BP. Likewise, no cuff is needed.

REFERENCES TO PRIOR ART

U.S. Pat. No. 5,316,008 May 1994 Suga et al
U.S. Pat. No. 5,649,543 July 1997 Hosaka et al
U.S. Pat. No. 5,857,975 January 1999 Golub
U.S. Pat. No. 6,485,431 November 2002 Campbell
U.S. Pat. No. 6,561,986 May 2003 Baura et al.
U.S. Pat. No. 7,670,295 March 2010 Sackner et al.
2005/0222514 October 2005 Stigo
2011/006642 March 2011 Pandia et al.
2016/9307915 April 2016 McCombie et al.

The invention consists of:

1. A non-grip-type device containing a microprocessor, analog front end, memory, and also containing:

a first photoplethysmographic sensor, (PPG) positioned in a manner to take a first measurement by being placed in contact with an area of skin of a hand of a user at a preferred first measurement site on said hand, which measurement site is a thumb tip or index fingertip, with associated circuitry capable of identifying and characterizing a first pulse wave data stream;

a second PPG positioned in a manner to take a second PPG measurement by being placed in contact with an area of skin of the user, at a preferred second measurement site on the same hand as the first measurement site, which second measurement site is any fingertip not used as the aforementioned first measurement site, and which said second PPG is not required to be spaced apart at a predetermined distance from the first PPG, along with associated circuitry and logic, capable of identifying and characterizing a second pulse wave data stream synchronized to said first pulse wave data stream, which positioning permits both the first and second PPGs being in contact with the first and second preferred measuring sites at the same time;

a timer and logic used by said microprocessor to measure the timing of characteristics of said first pulse wave data stream at the first PPG, and also to measure the timing of characteristics of said second pulse wave data stream at the second PPG, said characteristics including but not limited to the arrival time of said first and second pulse wave data streams, which said arrival time of the first and second pulse wave data streams is synchronized, and to calculate therefrom an arrival time difference between said first and second PPGs for a specific single heart beat, and to evaluate said arrival time difference for said single heart beat to calculate the blood pressure of said user;

wherein said memory stores a continuous stream of said characteristics from the first PPG and the second PPG for a duration extending beyond a single heart beat, to a duration of a plurality of heart beats;

wherein said logic additionally measures amplitude characteristics of said first and second pulse wave data streams;

wherein said first PPG and said second PPG are positioned in proximity to each other on the surface of said device, such that the first and second measurement sites are at the same elevation with respect to the heart of the user at the time of measurement, thus obviating error due to dissimilar effects of gravity on the arrival times of said first and second pulse wave data streams.

* * * * *